(12) United States Patent
Adriansens et al.

(10) Patent No.: US 7,806,680 B2
(45) Date of Patent: *Oct. 5, 2010

(54) INSTALLATION FOR PRODUCING STERILE BOTTLES BY BLOW MOLDING STERILIZED PREFORMS

(75) Inventors: Eric Adriansens, Octeville sur Mer (FR); Stéphane Hebert, Octeville sur Mer (FR)

(73) Assignee: Sidel Participations, Octeville-sur-Mer (FR)

( * ) Notice: Subject to any disclaimer, the term of this patent is extended or adjusted under 35 U.S.C. 154(b) by 417 days.

This patent is subject to a terminal disclaimer.

(21) Appl. No.: 11/922,573

(22) PCT Filed: Jun. 6, 2006

(86) PCT No.: PCT/EP2006/063002

§ 371 (c)(1),
(2), (4) Date: Dec. 20, 2007

(87) PCT Pub. No.: WO2006/136498

PCT Pub. Date: Dec. 28, 2006

(65) Prior Publication Data

US 2009/0081326 A1    Mar. 26, 2009

(30) Foreign Application Priority Data

Jun. 24, 2005   (FR) .................................. 05 51751

(51) Int. Cl.
*B29C 49/68* (2006.01)
*B65B 55/06* (2006.01)
*B65B 55/10* (2006.01)

(52) U.S. Cl. ...................................... 425/526; 422/304
(58) Field of Classification Search ................. 422/303, 422/304; 425/526
See application file for complete search history.

(56) References Cited

U.S. PATENT DOCUMENTS

| 3,087,209 | A  | * | 4/1963  | Monk ......................... 422/304 |
| 6,562,281 | B1 |   | 5/2003  | Marchau et al. |
| 6,692,684 | B1 |   | 2/2004  | Nantin et al. |
| 6,808,681 | B2 | * | 10/2004 | Bjerborn ....................... 422/28 |
| 2001/0010145 | A1 | * | 8/2001 | Tawa et al. .................... 53/425 |
| 2008/0152538 | A1 | * | 6/2008 | Quetel et al. ................... 422/28 |
| 2010/0047120 | A1 | * | 2/2010 | Adriansens et al. ........... 422/22 |

FOREIGN PATENT DOCUMENTS

| DE | 43 05 478 | 8/1994 |
| EP | 0 894 543 | 2/1999 |

* cited by examiner

*Primary Examiner*—Robert B Davis
(74) *Attorney, Agent, or Firm*—Young & Thompson

(57) ABSTRACT

An installation producing sterile bottles by blow molding starting from preforms (12), includes a sterilizing treatment unit (26), a thermal conditioning unit, a molding unit, where the sterilizing treatment unit (26) includes an atomizing device (36) provided with a nozzle (38) which sprays, onto each preform (12), in laminar-flow form, a stream (F) of vaporized sterilizing product at the interior of the preform (12) and along a mean axis of spraying (A2) of the nozzle (38), where this axis is generally parallel to the axis (A1) of the preform (12) during treatment and is radially off-center with regard to the axis (A1) of the preform (12).

13 Claims, 3 Drawing Sheets

INSTALLATION FOR PRODUCING STERILE BOTTLES BY BLOW MOLDING STERILIZED PREFORMS

The invention relates to an installation producing sterile bottles by blow molding starting from plastic preforms.

The invention more particularly relates to an installation producing sterile bottles by blow molding starting from plastic preforms, where the preforms are conveyed to the interior of the installation in a continuous stream which flows from upstream to downstream, including:

- a sterilizing treatment unit including an atomizing device provided with at least one nozzle which sprays a stream of sterilizing product in the form of a jet of vapor towards the neck of each preform during treatment, with the aim of sterilizing at least the internal walls of the preform,
- a thermal conditioning unit, including at least one oven which heats the preforms,
- a molding unit including at least one mold and at least one blow-molding device which subjects each preform to internal overpressure in such a way that it assumes the shape of the mold cavity, producing a bottle.

The document US-A-2001/0010145 describes an example of an installation of this type intended for producing sterile bottles by blow molding starting from sterilized preforms.

That type of installation has the disadvantage of requiring a throughput of sterilizing product and/or an injection pressure of sterilizing product of considerable magnitude to succeed in covering completely the internal walls of the preforms so as to sterilize the interior of the preforms completely.

Consequently, the installation consumes a considerable amount of sterilizing product and the sterilization operation is costly.

That type of installation is more particularly described and shown in the document WO-A2-99/03667, which relates to a process and an installation for the manufacture of sterile plastics containers.

The installation includes a device for supplying the preforms to means of heating, and upstream of this device the preforms are treated, at least in the interior of the preforms, by means of sterilization. The means of sterilization particularly comprise a sterilization product, such as a chemical solution of hydrogen peroxide ($H_2O_2$) which is thermally activatable, particularly by the heat from the means of heating.

The means of sterilization include, for this purpose, a sprayer made from a spray gun, which permits wetting of the interior of the preforms with sterilization product which is "cold", i.e. has not undergone any prior heating and which is liquid.

The sterilization product is then activated by the effect of the heat before it evaporates.

In the installation described in that document, the gun is typically a bi-fluid gun.

This term is used because the spray gun includes a liquid nozzle and an air nozzle forming a circular spray system which can be placed over the path of the preforms so as to spray atomized sterilization product.

The atomized sterilization product is formed from a cloud of droplets which is sprayed by the spray gun towards the interior of the preform in turbulent flow.

A flow is defined as "turbulent" when the Reynolds number R is, for example, greater than the critical Reynolds number Rc=2000 and, conversely, is defined as "laminar" when the Reynolds number R is lower than the critical Reynolds number Rc=2000.

It will be recalled that the Reynolds number R is defined by the formula:

$$R = Ux/v$$

where "U" corresponds to the mean flow velocity, "x" is a linear reference dimension—such as the diameter "d" for example—and "v" is the coefficient of kinematic viscosity of the fluid, which is equal to the quotient obtained by dividing the coefficient of viscosity by the density of the fluid.

It has been found that this type of turbulent flow of sterilization product or sterilizing product to the interior of the preform leads to formation of a collection of droplets which are not homogeneously distributed on the internal wall of the preform.

This occurs because use of a spray gun is particularly characterized by a considerable throughput of sterilizing product which is obtained by compressing a gas, an example being compressed air at pressures of about 2 to 3 bar, thus producing turbulent flow.

Now, turbulent flow leads to inhomogeneous deposition of residual droplets of sterilizing product on the internal walls of the preforms. Furthermore, the droplets of sterilizing product form an excess of material which is not entirely vaporized during the heating process.

These droplets of sterilizing product firstly bring about local etching of the material of the preform, generally composed of polyethylene terephthalate (PET), and secondly, during the heating of the preforms, act as magnifiers for thermal radiation, the result being markings on the walls of the bottles derived from the preforms concerned.

These markings on the walls of the bottles are a visual defect in the product, which is also sometimes termed "orange peel appearance".

The present invention is particularly aimed at mitigating these disadvantages, and more particularly at enabling the desired degree of sterility to be obtained at least on all of the internal wall and on the neck of the preform and allowing production of bottles particularly free from the "orange peel" visual defect.

To this end, the invention provides an installation of the type described above, characterized in that the mean axis of spraying of the nozzle is generally parallel to the axis of the preform during treatment and is radially off-center with regard to the axis of the preform, and in that the form in which the stream of sterilizing product is sprayed at the interior of the preform is that of laminar flow.

By virtue of the spraying of the stream of sterilizing product in the form of laminar flow, for example starting from a hot mixture of product vapor such as that of hydrogen peroxide ($H_2O_2$) and air, homogeneous distribution of the sterilizing product is obtained on the internal wall of the preform, and the risk of "orange peel" visual defect is thus eliminated.

However, as a function of the profile of the internal walls of each preform, it is not possible to be sure of reaching the base of the preforms when using laminar flow.

The reason for this is that when a laminar flow of sterilizing product is sprayed into a preform, particularly one whose diameter is low and which is very long, this specific type of flow generates a plug of stagnant air or an "overpressure" in the base of the preform, and this adversely affects uniform condensation of the sterilizing product.

By virtue of the offset E of the axis of spraying of the nozzle with regard to the axis of the preform, the laminar flow of sterilizing product condenses uniformly on the entirety of the internal wall of the preform, including the area within the base.

The problem of formation of this type of overpressure plug is therefore advantageously solved, and all of the internal wall of the preform and of the neck is entirely satisfactorily sterilized by the laminar flow of sterilizing product.

In some other characteristics of the invention:
the axis of spraying is off-center to the extent of at least nineteen percent of the value of the internal diameter of the opening delimited by the neck;
the axis of spraying is off-center to the extent of at most thirty-two percent of the value of the internal diameter of the opening delimited by the neck;
in the sterilizing treatment unit, the preforms are generally aligned in a longitudinal running direction, and are arranged upright parallel to, and alongside, one another, and the axis of spraying of the nozzle is radially offset in an approximately orthogonal direction with regard to the running direction;
the form of the stream of sterilizing product produced by the nozzle is generally that of a vertical curtain;
the atomizing device is provided with a plurality of nozzles which are generally aligned longitudinally, and the axes of spraying of the nozzles are approximately parallel;
the sterilizing product is made from a compound containing hydrogen peroxide, or is made from vaporized hydrogen peroxide, which is activated by heating beyond an activation temperature;
the hydrogen peroxide is activated by heating in the interior of the oven of the thermal conditioning unit by heating of the preform to a temperature above the activation temperature;
the hydrogen peroxide is activated in the sterilizing treatment unit by spraying onto the preform previously heated to a temperature above the activation temperature;
the hydrogen peroxide is sprayed at a temperature above one hundred and six degrees Celsius, for example a temperature in the vicinity of one hundred and ten to one hundred and twenty degrees Celsius.

Other characteristics and advantages of the invention will be apparent from reading the detailed description that follows, understanding of which will be aided by reference to the annexed drawings, in which.

In the description below, identical references will be used to indicate similar or identical elements.

Figure 1:
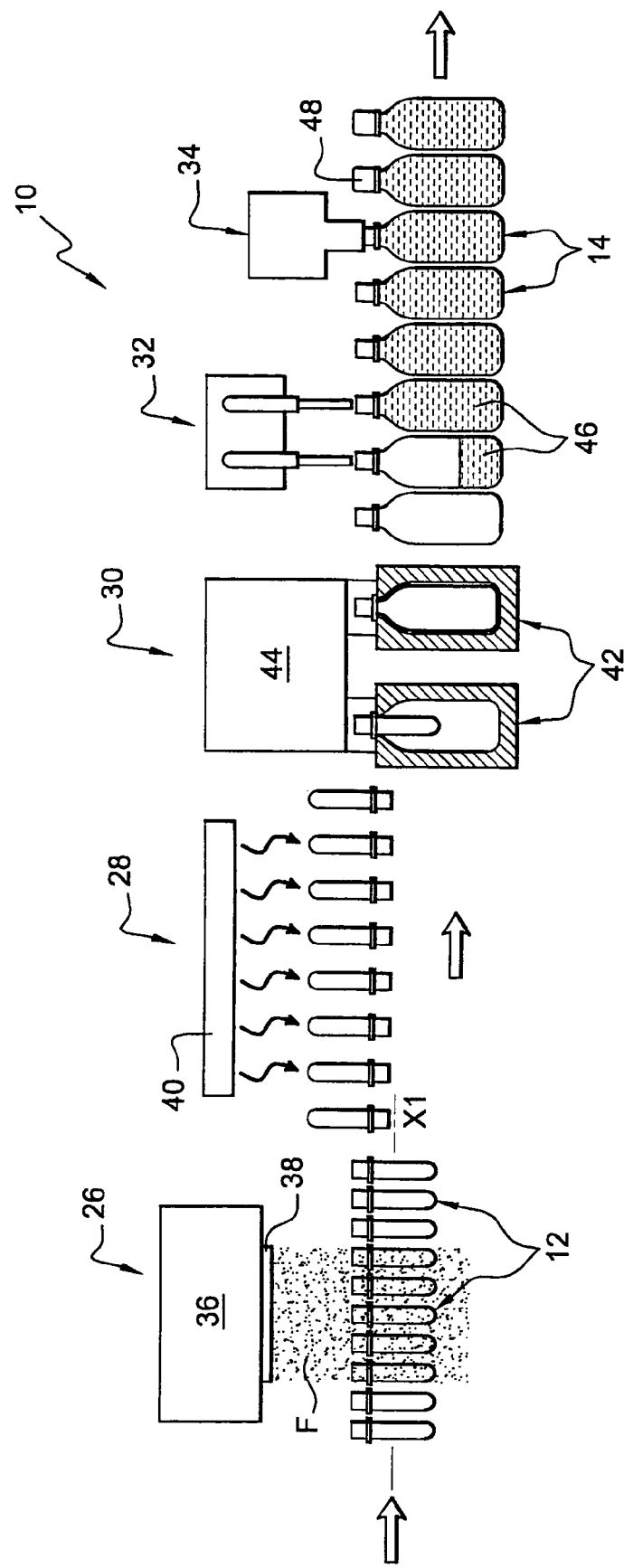
FIG. 1 is a diagram which represents a first exemplary embodiment in an installation producing bottles by blow molding and including a sterilization unit complying with the teaching of the invention.

FIG. 1 shows an installation 10 producing bottles 14 by blow molding starting from plastic preforms 12.

This type of installation 10 is used, for example, for the manufacture of plastics bottles 14 such as polyethylene terephthalate (PET) bottles.

Each preform 12 generally has the shape of a tube which is closed at one end and whose other end already has the final shape of the neck 16 of the bottle 14.

Figure 2:
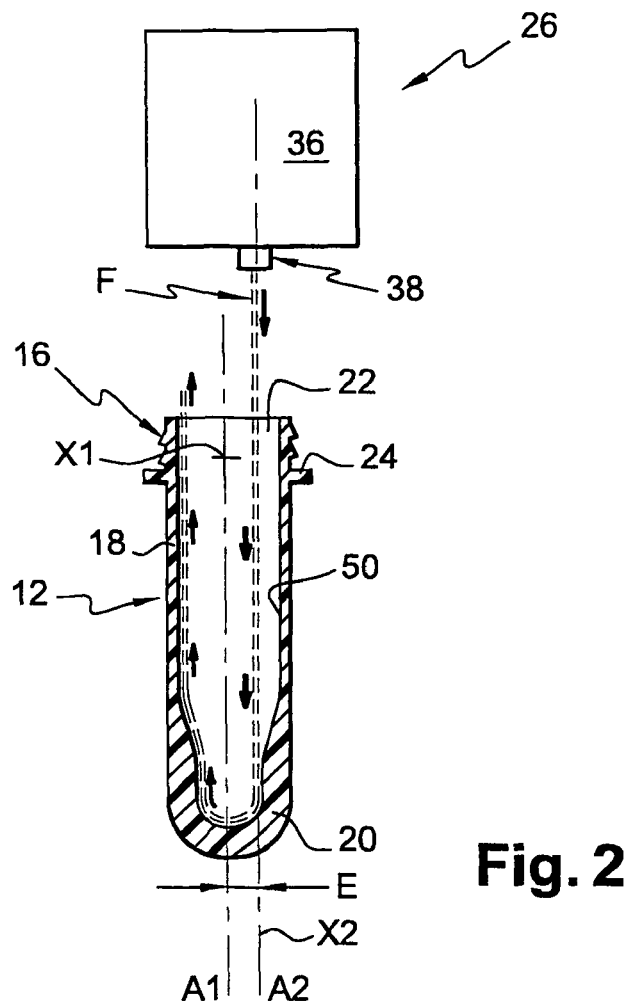
FIG. 2 is an axial-section view in the plane of section 2-2 which represents diagrammatically a preform in the sterilization unit of the installation of FIG. 3.

FIG. 2 shows a non-limiting preform 12 with vertically extending axis A1 of its cylindrical body 18.

The axis A1 of the body 18 is the same as the axis of the neck 16.

The lower end 20 of the preform 12 is closed, while its upper end forms the neck 16 which delimits an opening 22 and which is provided here with a radial external flange 24.

The preforms 12 have been previously produced by an injection-molding process.

The preforms 12 are conveyed to the interior of the installation 10 in a continuous stream which flows from upstream to downstream, i.e. from left to right in FIG. 1.

In the first example, represented in FIG. 1, the installation 10 includes, from upstream to downstream, a "sterilizing treatment" unit 26, preferably including means of preparation of the sterilizing product, a thermal conditioning unit 28, and a molding unit 30.

The installation 10 advantageously also includes, following the molding unit 30, a filling unit 32 and a sealing unit 34.

The sterilizing treatment unit 26 includes an atomizing device 36 provided with at least one nozzle 38 which sprays, towards the neck 16 of each preform 12 during treatment, a stream F of sterilizing product in such a way as to produce bottles 14 asepticized or sterile as required by the applications.

The sterilizing treatment unit 26 will be described in more detail below in relation to the characteristics of the invention.

The thermal conditioning unit 28 includes at least one oven 40 which heats the preforms 12 to a temperature appropriate for molding.

The molding unit 30 includes at least one mold 42 and at least one blow-molding device 44 which subjects each preform 12 to internal overpressure in such a way that it assumes the shape of the mold cavity 42, producing a bottle 14.

The molding unit 30 can also include means of elongation (not shown) which stretch the preform 12 towards the base of the mold 42, during the molding operation.

The filling unit 32 injects the product 46 to be packaged into the bottles 14 derived from the molding unit 30, and then the sealing unit 34 hermetically seals the filled sterile bottles 14, for example using an appropriate cap 48, or alternatively a cover and/or a cork.

A more detailed description will now be given of a preferred embodiment of the sterilizing treatment unit 26 of the invention.

The sterilizing product is preferably made from a compound containing hydrogen peroxide, or is made from vaporized hydrogen peroxide ($H_2O_2$), which is sprayed towards the preforms 12 in the form of a jet of gas including sterilizing product in the vapor state, advantageously a jet of dry vapor.

To this end, the means (not shown) of preparation of the sterilizing product of the sterilizing treatment unit 26 particularly include means of heating (not shown) of the sterilizing product and a source of air (not shown), advantageously compressed and/or sterilized by any appropriate means, this source being provided to propel the sterilizing product through the nozzle 38 of the atomizing device 36.

The compressed air is advantageously dehydrated and circulates at low velocity, its flow being directed so as to provide a carrier for the vapor of the sterilizing product.

The concentration of sterilizing product in the vapor is, for example, approximately equal to twenty-five percent.

At the exit from the nozzle 38, the vapor containing the sterilizing product reaches a given temperature T appreciably higher than the vaporization temperature of the sterilizing product.

If hydrogen peroxide ($H_2O_2$) is used, the temperature T at the exit from the nozzle is advantageously higher than one hundred and six degrees Celsius (106° C.), preferably between one hundred and ten degrees Celsius (110° C.) and one hundred and twenty degrees Celsius (120° C.).

When this vapor comes into contact with the internal walls 50 of the preforms 12, which are relatively cold, the sterilizing product condenses in the form of a mist, in such a way that a film of sterilizing product is deposited on the entirety of the preform 12, in particular on the internal walls 50 of the preforms 12, which are thus covered with a mist forming a film of sterilizing product.

The sterile product is therefore advantageously deposited by condensation to give an appreciably uniform film which, unlike in the prior art, can eliminate any risk of marking and of "orange peel" appearance.

The preforms 12 then pass into the thermal conditioning unit 28 including the heating oven 40 for reheating of the preforms 12 to a temperature higher than or equal to the molding temperature, so that the blow-molding operation can then be carried out.

The molding temperature depends, of course, on the type of preform 12, which is a function of the applications, and by way of example the temperature is between ninety five degrees Celsius (95° C.) and one hundred and thirty-five degrees Celsius (135° C.).

Sterilization is now achieved by raising the temperature of the preform 12 covered by the film of mist of sterilizing product beyond an "activation temperature".

The activation temperature of hydrogen peroxide ($H_2O_2$) starts, for example, at about seventy degrees Celsius (70° C.), i.e. here a temperature below the molding temperature.

Passage of the preforms 12 into the thermal conditioning unit 28 advantageously therefore activates the sterilizing product by heat, and this has an immediate bactericidal effect on the internal walls 50 of the preforms 12.

This type of heating oven 40 for preforms includes, in a known manner (not shown), a longitudinal heating tunnel, along which the preforms 12 are transported by a transport device between a first end of the tunnel where the preforms 12 are generally cold when they enter, before they emerge again, heated or reheated, through the second end of the tunnel, and are ready for the blow-molding operation.

To ensure deep heating of a preform 12, i.e. of the lower end 20 forming the base as well as the cylindrical wall of the body 18, the preforms 12 are generally self-rotated during their circulation through the oven 40 by means of a transport device including means of prehension, for example of the type described in the document WO-A-00/48819.

Furthermore, one wall of the tunnel is equipped with means of radiative heating, while the other wall is provided with aeration apertures to permit passage of blown air in order to promote homogeneous heating within the entire thickness of the preform 12 without overheating the layer of material at the surface.

This is achieved in that the blown air can remove the convective heat generated by the means of heating, thus giving preference to penetration of the radiation that they produce into the thickness of the material from which the preform 12 is made.

For further details of these ovens 40 for heating of preforms, reference may be made, for example, to the documents EP-A-0,620,099 and EP-A-0,564,354.

Meanwhile, in the case of an installation 10 such as that shown in FIG. 1, the air blown onto the preforms 12 in the oven 40 removes all or part of the film of mist of sterile product previously deposited on the exterior of the preform 12 by condensation in the sterile treatment unit 26.

Preforms 12 whose interior is mainly sterile are thus obtained at the outgoing end of the oven 40.

A logarithmic reduction in the number of germs of the order of 3D, or 3 log, equivalent to 1000 ($10^3$) is obtained by virtue of an installation 10 as in the first exemplary embodiment.

The numerical quantity of germs is determined, for example, by a known method of counting after washing, filtration and culturing.

The oven 40 advantageously includes means of protection particularly to limit corrosion of the parts or sections exposed to the sterile product on which air is blown within the tunnel.

In one embodiment (not shown) of the installation 10, a sterile confinement enclosure can be provided to permit completely aseptic treatment of the preforms 12 and of the bottles 14.

Figure 3:
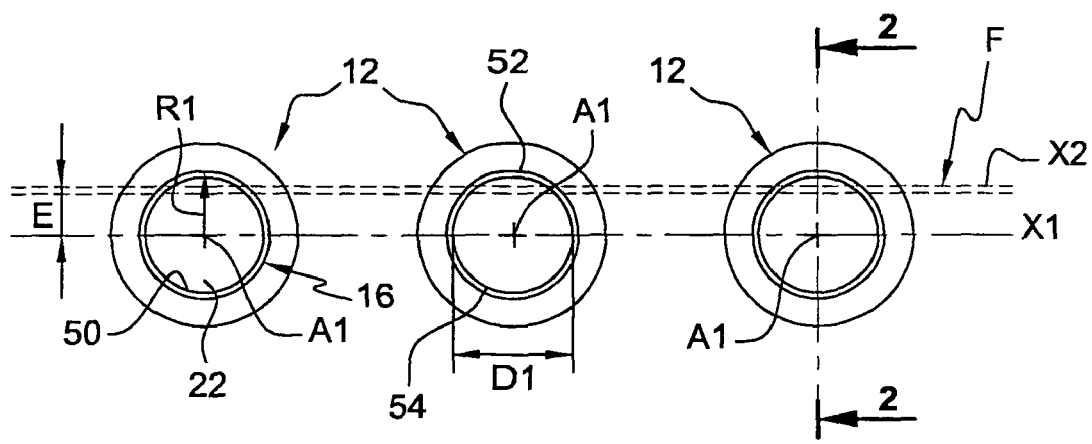
FIG. 3 is a plan view which represents a series of preforms in the sterilization unit.

In the embodiment represented here, particularly in FIG. 3, the preforms 12 are aligned in vertical position, following a longitudinal horizontal running direction, "direction X1", with the neck 16 upwards, when they run into the sterilizing treatment unit 26.

The running direction X1 passes through the axes A1 of the preforms 12 during treatment.

In accordance with the teaching of the invention, the mean axis A2 of spraying of the nozzle 38 is generally parallel to the axis A1 of each preform 12 during treatment and it (A2) is radially off-center, by a specific amount of offset E, with regard to the axis A1 of the preform 12, and the form in which the stream F of sterilizing product is sprayed at the interior of the preform 12 is that of laminar flow.

It is preferable that the mean axis A2 of spraying, which here is vertical, is off-center along an interior radius R1 of the neck 16 which is orthogonal to the running direction X1.

As an alternative, the mean vertical axis A2 of spraying is off-center along an interior radius R of the neck 16 which is parallel to the longitudinal running direction X1, or which forms a specified angle θ with said longitudinal running direction X1.

The shape of the nozzle 38 advantageously permits a stream F of sterilizing product to be sprayed towards the bottom generally in the form of laminar flow, i.e. in the form here of a vertical and preferably longitudinal curtain.

To this end, the nozzle 38 advantageously includes a longitudinal or circular slot, or as an alternative, for example, a generally circular hole for spraying of the stream F.

The laminar flow F here generally extends in a vertical longitudinal plane, "spray plane" X2, which is offset radially with regard to the running direction X1, by a distance equal to the offset E.

The stream F of sterilizing product here can comprise an infinite number of mean axes A2 of spraying which extend vertically within the spray plane X2.

It is preferable that the offset E is between a minimum value Emin approximately equal to nineteen percent of the internal diameter D1 of the neck 16 of each preform 12 and a maximum value Emax approximately equal to thirty-two percent of the internal diameter D1 of the neck 16.

In an advantageous embodiment, the offset E chosen is fixed and approximately equal to eight millimeters, therefore being appropriate for types of preform 12 whose internal diameters D1 are between about twenty-five and forty-two millimeters.

By virtue of the arrangement of the nozzle 38 of the invention, the stream F of sterilizing product is approximately flush with one first sector 52 of the internal wall 50 of each preform 12, and the stream F of sterilizing product therefore impacts said sector 52 of the internal wall 50.

On arriving at the lower end 20 of the preform 12, the stream F of sterilizing product slides across the base of the preform 12 and ascends again over a second sector 54 of internal wall 50 diametrically opposite to the first sector 52.

The stream F of sterilizing product thus generally covers the entirety of the internal wall 50 of each preform 12 by laminar flow.

The arrangement of the invention particularly permits prevention of creation of a plug of overpressure in the base of the preforms 12, which would prevent the sterilizing product from reaching the base.

In particular, the velocity of propulsion of the sterilizing product at the exit from the nozzle 38 is sufficiently low to obtain laminar flow, for example of the order of from 0.3 to 0.5 m/s with a nozzle of length about 35 mm and of calibrated diameter about 3 mm.

It will be noted that the stream F of sterilizing product creates a mist of sterilizing product which becomes diffused around the stream F, thus particularly enabling the sterilizing product to become deposited on the entirety of the internal wall 50 of each preform 12.

Furthermore, this mist also becomes deposited on the exterior wall of the neck 16, thus permitting simultaneous asepticization or sterilization of the internal wall 50 and the neck 16 of each preform 12.

Figure 4:
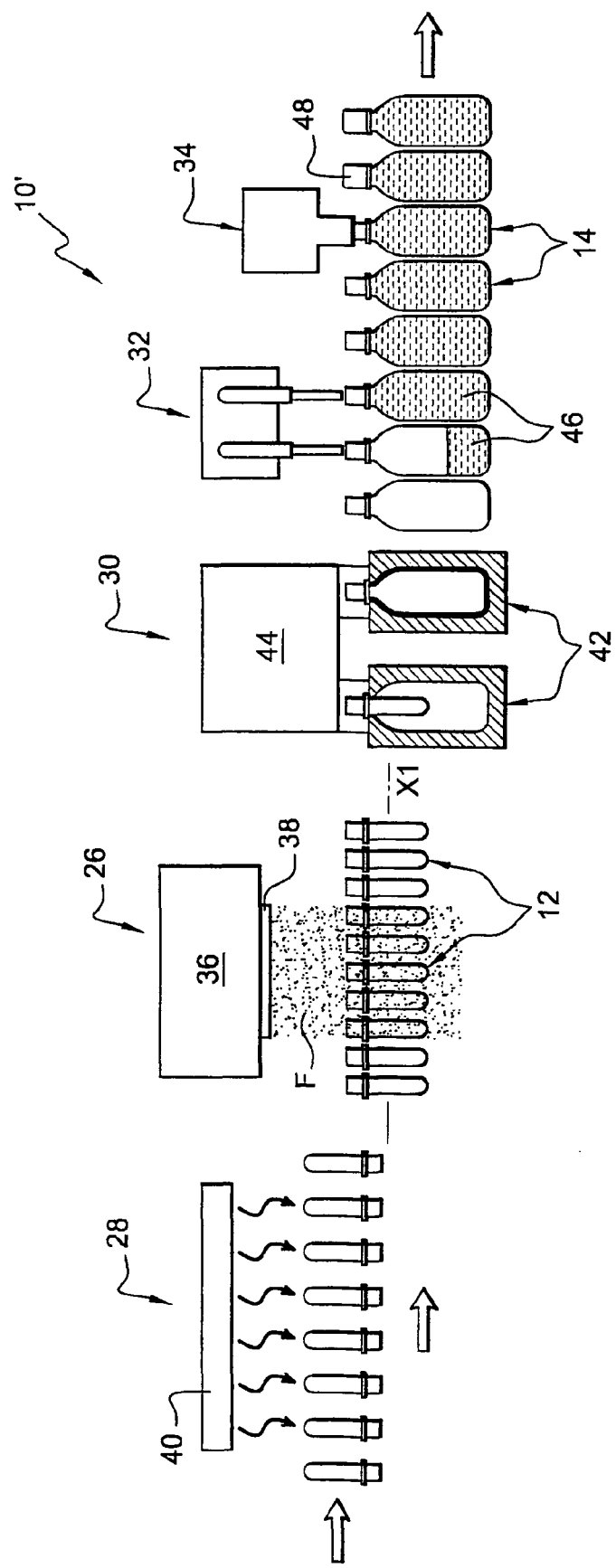
FIG. 4 is a diagram which represents a second exemplary embodiment in an installation producing bottles by blow molding and including a sterilization unit complying with the teaching of the invention.

FIG. 4 shows a second exemplary embodiment of the invention in an installation 10' producing sterile bottles by blow molding which, like that of FIG. 1, will be described below by comparison.

The installation 10' of FIG. 4 differs in essence in the inversion carried out between the thermal conditioning unit 28 and the sterilizing treatment unit 26.

The installation 10' therefore includes, respectively from upstream to downstream, a thermal conditioning unit 28, a sterilizing treatment unit 26 and a molding unit 30.

The units 26, 28 and 30 here are analogous to those of FIG. 1.

The preforms 12 are therefore first heated by the thermal conditioning unit 28 by being taken to a temperature above or equal to the molding temperature, for example between ninety-five degrees Celsius (95° C.) and one hundred and thirty-five degrees Celsius (135° C.).

The preforms 12 thus heated then pass through the sterilizing treatment unit 26, where they are sterilized.

Since the preforms 12 here are at a temperature above the activation temperature, for example of the order of about seventy degrees Celsius (70° C.) for hydrogen peroxide ($H_2O_2$), there is no condensation as previously produced and therefore no deposition of a uniform film of mist of sterilizing product.

This is achieved because the sterilizing product is instantly activated and evaporates on contact with the heated preform 12, then producing a similar bactericidal effect on the entirety of the preform 12, i.e. not only on the internal wall 50 but also on the external parts of the preform 12.

By virtue of the installation 10' of FIG. 4, the preforms 12 are therefore entirely sterilized, and this gives degrees of sterilization of the order of 6 log, i.e. above those obtained with the installation 10 of FIG. 1.

The oven 40 of the thermal conditioning unit 28 is advantageously a conventional oven which, being upstream of the sterilizing treatment unit, is not exposed, as previously, to risks of corrosion by the sterilizing product, and does not therefore require any particular supplementary means of protection.

The preforms 12 passing through the installation 10 or 10', particularly the sterilizing treatment unit 26, are vertically oriented here with the neck 16 upwards, i.e. in "neck-upwards" position.

As an alternative, the preforms 12 are vertically oriented for the sterilizing treatment unit 26 with the neck 16 downwards, or "neck-downwards", and the preforms 12 can change vertical orientation within the installation 10, 10', in particular from one unit to the next.

The invention has been described with an atomizing device 36 advantageously including a nozzle 38 in the form of a longitudinal or circular slot. In alternative embodiments (not shown), the stream F of sterilizing product can, of course, be achieved by a plurality of tubular nozzles 38 aligned along the spray plane X2.

It will be noted that the installations 10 and 10' have been shown with aligned treatment units 26, 28, 30, 32, 34 by way of illustration, but these treatment units can be arranged in a different configuration.

Certain treatment units 26, 28, 30, 32, 34 can use rotating devices such as carousels (not shown).

What is claimed is:

1. An installation (10, 10') producing sterile bottles (14) by blow molding starting from plastic preforms (12), where the preforms (12) are conveyed to the interior of the installation (10, 10') in a continuous stream which flows from upstream to downstream, including:
    a sterilizing treatment unit (26) including an atomizing device (36) provided with at least one nozzle (38) which sprays a stream (F) of sterilizing product in the form of a jet towards the neck (16) of each preform (12) during treatment, with the aim of sterilizing at least the internal walls (50) of the preform (12),
    a thermal conditioning unit (28), including at least one oven (40) which heats the preforms (12),
    a molding unit (30) including at least one mold (42) and at least one blow-molding device (44) which subjects each preform (12) to internal overpressure in such a way that it assumes the shape of the mold cavity (42), producing a bottle (14),
    characterized in that the mean axis (A2) of spraying of the nozzle (38) is generally parallel to the axis (A1) of the preform (12) during treatment and is radially off-center with regard to the axis (A1) of the preform (12), and in that the form in which the stream (F) of sterilizing product is sprayed at the interior of the preform (12) is that of laminar flow.

2. The installation (10, 10') as claimed in claim 1, characterized in that the axis (A2) of spraying is off-center to the extent of at least nineteen percent of the value of the internal diameter (D1) of the opening (22) delimited by the neck (16).

3. The installation (10, 10') as claimed in claim 1, characterized in that the axis (A2) of spraying is off-center to the extent of at most thirty-two percent of the value of the internal diameter (D1) of the opening (22) delimited by the neck (16).

4. The installation (10, 10') as claimed in claim 1, characterized in that, in the sterilizing treatment unit (26), the preforms (12) are generally aligned in a longitudinal running direction (X1), and are arranged upright parallel to, and alongside, one another, and in that the axis (A2) of spraying of the nozzle (38) is radially offset in an approximately orthogonal direction with regard to the running direction (X1).

5. The installation (10, 10') as claimed in claim 4, characterized in that the form of the stream (F) of sterilizing product produced by the nozzle (38) is generally that of a vertical curtain.

6. The installation (10, 10') as claimed in claim 4, characterized in that the atomizing device (36) is provided with a plurality of nozzles (38) which are generally aligned longitudinally, and in that the axes (A2) of spraying of the nozzles (38) are approximately parallel.

7. The installation (10, 10') as claimed in claim 1, characterized in that the sterilizing product is made from a compound containing hydrogen peroxide, or is made from vaporized hydrogen peroxide, which is activated by heating beyond an activation temperature.

8. The installation (10) as claimed in claim 7, characterized in that the oven (40) of the thermal conditioning unit (28) is arranged to heat the preform (12) to a temperature above the activation temperature of the hydrogen peroxide.

9. The installation (10') as claimed in claim 7, characterized in that the sterilizing treatment unit (26) is arranged to spray the hydrogen peroxide onto the preform (12).

10. The installation (10, 10') as claimed in claim 7, characterized in that the sterilizing treatment unit is arranged to spray the hydrogen peroxide at a temperature above one hundred and six degrees Celsius.

11. The installation (10, 10') as claimed in claim 2, characterized in that the axis (A2) of spraying is off-center to the extent of at most thirty-two percent of the value of the internal diameter (D1) of the opening (22) delimited by the neck (16).

12. The installation (10, 10') as claimed in claim 5, characterized in that the atomizing device (36) is provided with a plurality of nozzles (38) which are generally aligned longitudinally, and in that the axes (A2) of spraying of the nozzles (38) are approximately parallel.

13. The installation (10, 10') as claimed in claim 9, characterized in that the sterilizing treatment unit is arranged to spray the hydrogen peroxide at a temperature above one hundred and six degrees Celsius.

\* \* \* \* \*